United States Patent [19]

Hammock et al.

[11] Patent Number: 5,098,706
[45] Date of Patent: Mar. 24, 1992

[54] JUVENILE HORMONE ESTERASE FOR INSECT CONTROL

[75] Inventors: Bruce D. Hammock; Matthew L. Philpott, both of Davis, Calif.

[73] Assignee: The Regents of the University of California, Berkeley, Calif.

[21] Appl. No.: 265,528

[22] Filed: Nov. 1, 1988

[51] Int. Cl.$^5$ .............................................. A01N 63/00
[52] U.S. Cl. ................................. 424/93 A; 424/94.6; 435/69.1; 435/948
[58] Field of Search ....................... 424/94.1, 94.6, 93; 435/69.1, 948

[56] References Cited

U.S. PATENT DOCUMENTS 4,745,051  5/1988  Smith et al. ............................ 435/68
4,762,547  8/1988  Jwosaki et al. ..................... 424/94.6

FOREIGN PATENT DOCUMENTS 2074868  11/1981  United Kingdom ............... 424/94.6

OTHER PUBLICATIONS

Chem. Abstracts vol. 102, Entry 76006b.
Abdel-Aal et al., "Transition State Analogs as Ligands for Affinity Purification of Juvenile Hormone Esterase", *Science*, vol. 233, pp. 1073-1076, 1986.
Cheung et al., "Micro-Lipid Droplet Encapsulation of *Bacillus thuringiensis* subsp. Israelensis, δ-Endotoxin for Control of Mosquito Larvae", *Appl. Environ. Microbiol.*, vol. 50, No. 4, pp. 984-988, Oct. 1985.
Hammock et al., "Strategies for the Discovery of Insect Control Agents", Chapter 12 in Steffens et al. (Eds.), *Biomechanisms Regulating Growth and Development*, USDA Beltsville Symposia vol. 12, Kluwer Academic Press, 1988.
Hammock et al., "Analysis of Juvenile Hormone Esterase Activity", Chapter 32, pp. 487-495, in Law et al. (Eds.), *Methods in Enzymology*, vol. III: *Steroids and Isoprenoids* (Part B), Academic Press, 1985.
Hammock et al., "Selective Inhibition of JH Esterases from Cockroach Hemolymph", *Pesticide Biochemistry and Physiology*, vol. 7, pp. 517-530, 1977.

*Primary Examiner*—Thurman K. Page
*Assistant Examiner*—Peter F. Kulkosky
*Attorney, Agent, or Firm*—Majestic, Parsons, Siebert & Hsue

[57] ABSTRACT

A method of controlling insects comprises administering juvenile hormone esterase during a larval stadium to disrupt normal development. The juvenile hormone esterase is preferably administered by infecting insects with a baculovirus including the gene for juvenile hormone esterase. The enzyme fatally disrupts the normal development of the host insects.

4 Claims, 2 Drawing Sheets

JUVENILE HORMONE ESTERASE FOR INSECT CONTROL

This invention was made with government support under NIH Grant No. ES-02710, NSF Grant No. GCB-85-18697, and USDA Grant No. 85-CRCR-1-1715.

FIELD OF THE INVENTION

The present invention relates to insect control, and more particularly to insect control by biochemically induced disrupted development.

BACKGROUND OF THE INVENTION

The lepidopteran family noctuidae includes some of the most destructive agricultural pests, such as the genera Heliothis. Spodoptera and Trichoplusia. For example, included in this family are the tobacco budworm (*Heliothis virescens*), the cotton leafworm (*Alabama argillacea*), the spotted cutworm (*Amathes c-nigrum*), the glassy cutworm (*Crymodes devastator*), the bronzed cutworm (*Nephelodes emmedonia*), the fall armyworm (*Laphygma frugiperda*), the beet armyworm (*Spodoptera exigua*) and the variegated cutworm (*Peridroma saucia*). Juvenile hormone esterase is responsible for the stage-specific metabolism of juvenile hormone in such insects.

Juvenile hormone and juvenile hormone esterase have been studied extensively in the lepidoptera. In the final larval growing stage of these insects, there is a rapid decline in the juvenile hormone titer which initiates the physiological and behavioral events preceding pupation and adult development. This decline in the juvenile hormone titer appears to be regulated by an increase in degradation by juvenile hormone esterase as well as a reduction of biosynthesis. Juvenile hormone esterase activity is very low in the early stadia of larval growth. Even at the peak activity levels in the blood of the final stadium, the concentration of juvenile hormone esterase has been estimated at less than 0.1 percent of the total protein. Yet the enzyme has a high affinity for juvenile hormone and has a rapid turnover. This means that juvenile hormone esterase should be extremely efficient at hydrolyzing juvenile hormone under biological conditions. The initial reduction in juvenile hormone titer in the last larval stadium initiates a sequence of events leading to pupation. Powerful and selective chemical inhibitors of juvenile hormone esterase have been used in vivo to demonstrate the developmental consequences of blocking the activity of juvenile hormone esterase. Treatment in the final larval stadium of the tomato hornworm (*Manduca sexta*), and other moth larvae with potent inhibitors can block almost all of the blood juvenile hormone esterase activity and cause a delay in the time of metamorphosis, presumably by allowing juvenile hormone to remain present.

A group of the chemical inhibitors of juvenile hormone esterase are the trifluoromethylketone sulfides, as described by U.S. Pat. No. 4,562,292, issued Dec. 31, 1985, inventors Hammock et al.

Until now, determining whether juvenile hormone esterase might elicit anti-juvenile hormone effects has remained untried. Classical methods of protein purification have been inefficient for the large-scale purification of juvenile hormone esterase because the esterase is in picomole amounts even at its peak levels. Recently, a purification method for juvenile hormone esterase from larval blood has been developed. Abdel-Aal and Hammock, *Science*, Volume 233, pp. 1073-1076 (1986).

SUMMARY OF THE INVENTION

It is an object of the present invention to provide uses of juvenile hormone esterase in insect control.

In one aspect of the present invention, a method of controlling insects is provided in which juvenile hormone esterase is administered to insects having a juvenile hormone dependency during a larval stadium to disrupt normal development thereof. Administration may be by means of a recombinant baculovirus that expresses juvenile hormone esterase in an infected host insect, although for some insects the juvenile hormone esterase itself may be encapsulated in lipid droplets and administered directly.

DETAILED DESCRIPTION OF THE PREFERRED EMBODIMENTS

Figure 1:
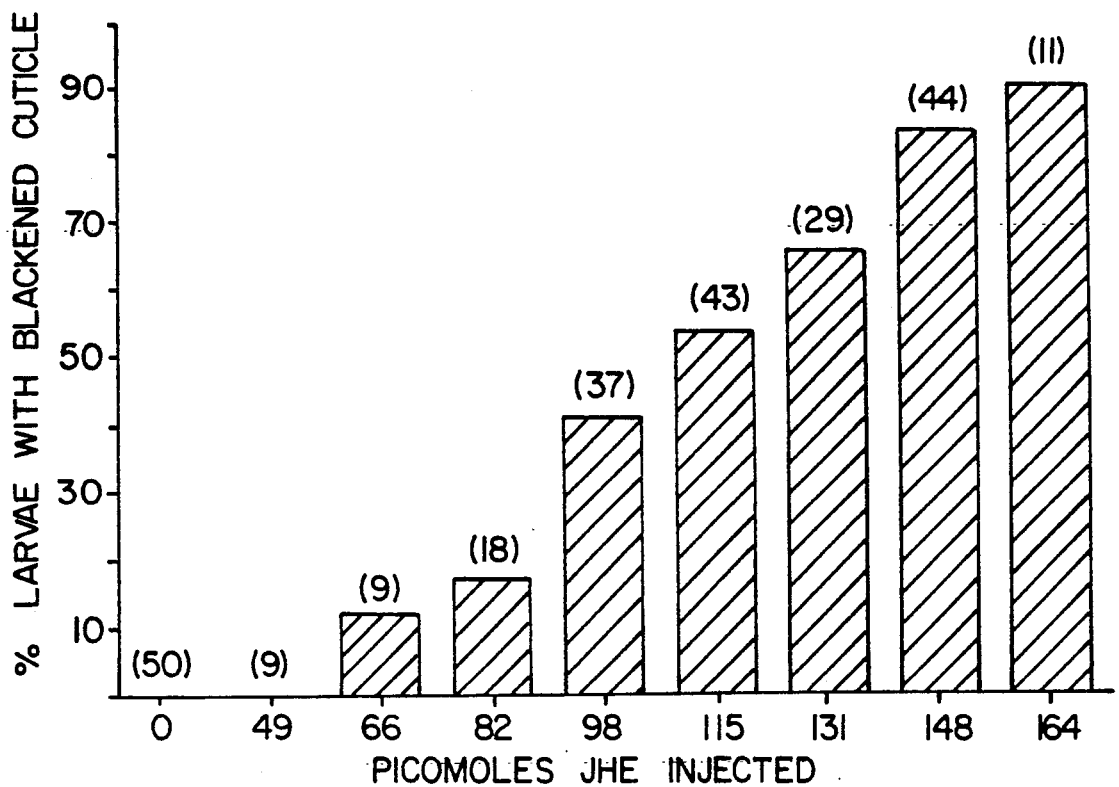
FIG. 1 illustrates a dose response of cuticular blackening for tomato hornworm larvae in the third stadium after administration of 49-164 pmoles of juvenile hormone esterase.

Juvenile hormone esterase is biochemically interesting in that it is an extraordinarily efficient enzyme. The very low $K_m$ 31 $6 \times 10^{-8}$M of juvenile hormone esterase, its high $k_{cat}$, and the low molarity of the enzyme even in the last larval stadium indicate that production of even small amounts of juvenile hormone esterase (<0.1% of total protein) should overpower the ability of the corpora allata to make juvenile hormone. This destruction of the juvenile hormone will be accelerated by the juvenile hormone hemolymph carrier protein. This carrier protects juvenile hormone at earlier stages of development, but it binds juvenile hormone less tightly than the esterase ($K_d = 6.1 \times 10^{-7}$M for *H. virescens*), and thus serves to accelerate degradation of juvenile hormone by juvenile hormone esterase by keeping juvenile hormone out of lipophilic depots.

Under $V_{max}$ conditions, the juvenile hormone esterase present in a single fifth stadium noctuid larva could hydrolyze over 100,000 times as much juvenile hormone each minute as is present in an entire larva at any time during development. Under physiological conditions, juvenile hormone esterase acts as an extremely large sink capable of extracting juvenile hormone from lipid depots and carriers by mass action and instantly inactivating it. Thus, precocious appearance of juvenile hormone esterase should reduce juvenile hormone titers, typically resulting in irreversible termination of the feeding stage of agriculturally destructive pests, such as the bollworm, and attempted pupation and death of the pest insect.

Because the substrate (juvenile hormone) readily penetrates membranes, the juvenile hormone esterase need only be expressed in a few cells to deplete juvenile hormone. Differential tissue depletion of juvenile hormone is likely to be even more rapidly fatal to an insect than uniform depletion.

Production of juvenile hormone esterase may be by cloning in a bacterium, as the gene for juvenile hormone esterase has been isolated and sequenced. This is described in copending application Ser. No. 265,507, filed concurrently herewith and incorporated by reference, inventors Hammock et al., entitled "Insect Diagnostic and Control Compositions". However, juvenile hormone esterase may also be obtained by affinity purification of the enzyme from insect blood, as will be more fully described by Example I. Since the juvenile hormone esterase coding sequence has ben determined as described in said application entitled "Insect Diagnostic and Control Compositions", methods to elicit the precocious expression of juvenile hormone esterase for insect control are now possible.

The recent development of a viral expression vector from a virus endemic in and selective for noctuid species permits practical field control systems for the Boll Worm and other insect pests. U.S. Pat. No. 4,745,051, issued May 17, 1988, inventors Smith et al., incorporated herein by reference, describes a method for producing a recombinant baculovirus expression vector capable of expression of a selected gene in a host insect cell.

Briefly, baculovirus DNA is cleaved to obtain a DNA fragment containing at least a promoter of the baculovirus gene. Preferably, this baculovirus gene is that coding for polyhedrin, since the polyhedrin protein is one of the most highly expressed eucaryotid genes known. The preferred baculovirus utilized is *Autographa californica,* although other baculovirus strains may be suitably utilized.

The method exemplified by U.S. Pat. No. 4,745,051 was used to express β-Interferon by infecting susceptible host insect cells with a recombinant baculovirus expression vector. However, a baculovirus may be modified by the method described by U.S. Pat. No. 4,745,051 but by utilizing the juvenile hormone coding sequence rather than the β-Interferon gene. A recombinant expression vector thus comprises a juvenile hormone esterase coding sequence under the control of a promoter sequence (preferably the polyhedrin promoter), which is deterologous with the juvenile hormone esterase coding sequence and which regulates the transcription thereof. Expression of the juvenile hormone esterase gene is accomplished by infecting susceptible host insect cells with a recombinant expression vector including a gene for juvenile hormone esterase to produce juvenile hormone esterase which, even at low levels, disrupts insect development when precociously appearing.

Figure 2:
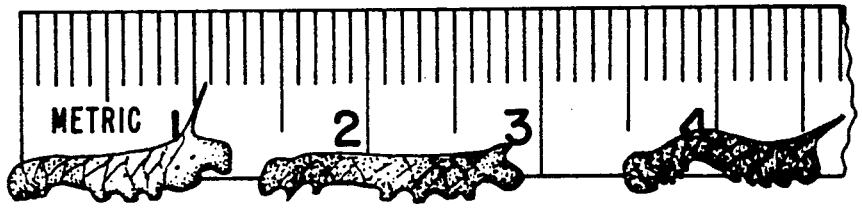
FIG. 2 illustrates third stadium tomato hornworm larvae after administration of 9 µg (148 pmoles) of juvenile hormone esterase as in FIG. 1, but then treated with 17 nmoles epofenonane, 0.17 nmoles epofenonane, or no epofenonane; and, FIG. 3 illustrates juvenile hormone esterase activity remaining in the blood after administration as in FIG. 1 eleven hours after the administration of three different amounts of the juvenile hormone esterase.

Juvenile hormone esterase is an insect protein which appears at critical times in the insect's life. It appears to present no risk to other groups of organisms. It is nonlethal to an individual cell which allows and perhaps encourages viral replication; yet the enzyme will fatally disrupt the normal development of the organism.

Administration of either the recombinant baculovirus or juvenile hormone esterase itself will typically be by oral ingestion. The baculovirus expressing juvenile hormone esterase may be admixed with known excipients, tabletting agents and the like, pelleted, and then scattered in the area needing control. Where administration is desired for larvae in water (e.g., mosquito larvae) then the juvenile hormone esterase itself may be encapsulated in micro-lipid droplets, or liposomes by methods known to the art.

EXAMPLE I

Blood collected from fifth stadium, day 4 hornworm larvae (25 mls) was then diluted 1:1 with phosphate buffer (pH 7.4, I=0.2 M) containing 5% sucrose, 0.05% nonionic surfactant (Triton-X100), 0.02% sodium azide, 0.01% phenylthiourea, $10^{-3}$ M mercaptoethanol (buffer cocktail). An affinity matrix (2-3 mls) was produced as in *Science,* 233. supra, was washed with buffer cocktail and shaken slowly with the diluted blood in an Econocolumn (Bio-Rad Laboratories) for 1 hour at room temperature. The affinity matrix was washed with buffer to remove contaminating proteins. This procedure was repeated 2–3 more times until the post-batching blood esterase activity dropped to 20% of precolumn activity. The affinity matrix was transferred to a 6 ml tuberculin syringe plugged with a disc of fritted polyethylene. The purified protein was shaken at $4^3$ C with 3-octylthio-1,1,1-trifluoropropanon-2-one (OTFP) $10^{-3}$ M elute the esterase, dialyzed against buffer cocktail to remove the OTFP, and concentrated using a Centricon 30 microconcentrator (Amicon) to 6 μg/μl.

EXAMPLE II

Tomato hornworm larvae, obtained from Zoecon Corp., were injected with the affinity purified juvenile hormone esterase obtained from Example I. Injections were performed at 10 hours after lights on the day before ecdysis to the third stadium. Larvae were reared on a 14L"10D photoperiod. Injections were made in 1.5 μl of buffer cocktail containing 3–10 μg (49–164 pmoles) of esterase. Total protein in each injection was kept constant at 10 μg with 6.6 μg/μl bovine serum albumen (BSA). Control injections in buffer contained 10 μg BSA or 12 μg larval blood protein from which the esterase was removed.

Similar effects were seen in the fourth stadium following injection into third stadium larvae. The effects were a cuticular blackening for the tomato hornworm larvae in a dose-responsive manner. Cuticular blackening is recognized as a sensitive indicator of juvenile hormone deficiency in the tomato hornworm and has been used to screen the biological activity of chemical anti-juvenile hormone agents.

The injections of juvenile hormone esterase into the second stadium tomato hornworm larvae caused a blackening of the cuticle after the molt to the third stage. The number of larvae with a blackened cuticle was clearly dependent on the amount of juvenile hormone esterase injected, as illustrated by FIG. 1. Second stadium larvae were chosen based on the assumption that the amount of protein required to produce an effect would be lowest in younger larvae, and from a practical standpoint, an anti-juvenile hormone agent is of best potential use for controlling insects the earlier it can disrupt development. In all cases where juvenile hormone esterase caused cuticular blackening, the larvae remained darker than normal throughout the third stadium. All fourth stadium larvae had the normal blue-green coloration.

FIG. 2 illustrates third stadium tomato hornworm larvae after injection with 9 μg (148 pmoles) of juvenile hormone esterase as in FIG. 1, but then treated with 17 nmoles epofenonane (left), 0.17 nmoles epofenonane (middle) or no epofenonane (right). As may be seen, the intermediate dose of epofenonane (0.17 nmoles) was not sufficient to prevent completely the blackening of the cuticle, but instead produced a localized effect by giving darkened larvae the appearance of wearing a green saddle. Epofenonane is a juvenile hormone chemical mimic, although it is not a substrate for juvenile hormone esterase. Thus, FIG. 2 illustrates that even a dose of juvenile hormone which is too low completely to prevent an anti-juvenile hormone effect can still effect a localized response.

Administrations of the juvenile hormone esterase at different times relative to the molt induced cuticular blackening to a greater or lesser degree, depending on the amount of juvenile hormone esterase administered. As has been demonstrated with other anti-juvenile hormone compounds, the ability to induce an anti-hormone response is dependent on well-defined, critical periods of sensitivity to juvenile hormone levels.

Figure 3:
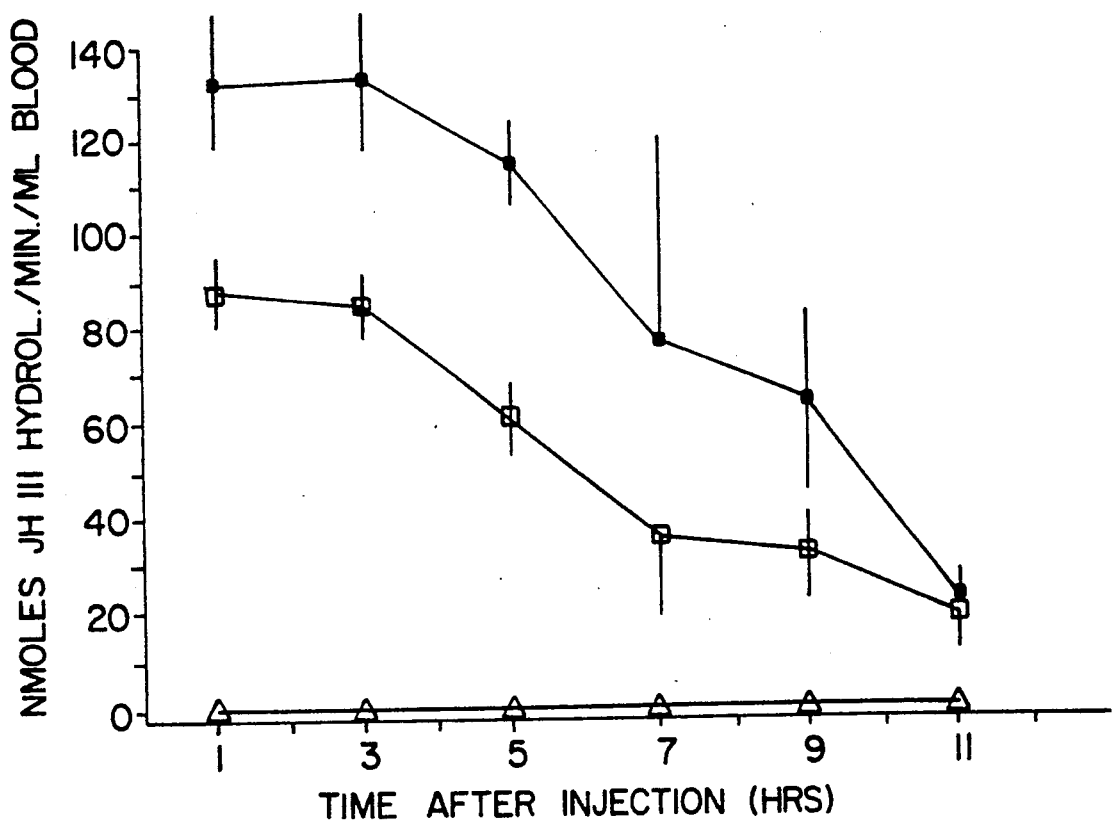

FIG. 3 illustrates how the actual level of juvenile hormone esterase activity in larvae correlates with the dose dependent effect that is induced. juvenile hormone esterase was administered as has been described, but with either 115 pmoles (upper curve) or 82 pmoles (middle curve) of the juvenile hormone esterase. Controls were injected with 9 µg bovine serum albumen (bottom curve). Thus, the esterase activity present in the hemolymph after injection was measured for two doses of the enzyme. Over the course of 11 hours after injection, the activity decreased with apparent half-lives of 6 hours (for the 82 picomole injection) and 9 hours (for the 115 picomole injection).

The picomole amounts of juvenile hormone esterase required to elicit an anti-juvenile hormone effect demonstrate that juvenile hormone esterase is a powerful anti-juvenile hormone agent. However, even a dose of juvenile hormone which is too low completely to provide an anti-juvenile hormone effect can still effect a localized response.

It appears that the ability to induce an anti-juvenile hormone effect when juvenile hormone biosynthesis is still active requires that the esterase remain sufficiently active to override biosynthesis and clear residual juvenile hormone throughout a critical period of juvenile hormone sensitivity. After the esterase activity drops below this threshold during the critical window, it cannot induce an anti-juvenile hormone effect. Therefore, administering a high dose of juvenile hormone esterase insures that the circulating level of activity stays above the threshold of activity in the critical period regardless of slight differences in staging the insects or in the administration technique.

In summary, the anti-juvenile hormone activity of juvenile hormone esterase has been demonstrated, and when made present by the means of expression as described herein will provide the continuous expression of juvenile hormone esterase and likewise the continual removal of juvenile hormone activity. This will ultimately prove injurious to the pest insect through death or disruption of normal development.

Although various aspects of the present invention have been described with respect to preferred embodiments thereof, it will be understood that the invention is entitled to protection within the full scope of the appended claims.

It is claimed:

1. A method for disrupting the normal development in or killing insects whose metamorphosis is regulated by juvenile hormone comprising:
   administering an anti-juvenile hormone agent to the insects, the administering effective to cause a precocious appearance of juvenile hormone esterase within the insects.

2. The method as in claim 1 wherein the anti-juvenile hormone agent includes a baculovirus, the administering is by infecting the insects with the baculovirus, the baculovirus having a gene capable of expressing juvenile hormone esterase within the infected insects.

3. The method as in claim 2 wherein the baculovirus is pelleted.

4. The method as in claim 1 wherein the anti-juvenile hormone agent administered is encapsulated.

* * * * *